(12) United States Patent
Alroy

(10) Patent No.: US 6,486,779 B1
(45) Date of Patent: Nov. 26, 2002

(54) EMERGENCY SIGNALING OR DIAGNOSTIC DEVICE

(75) Inventor: Yoram Alroy, Tel Aviv (IL)

(73) Assignee: SHL Telemedicine International Ltd., Tel Aviv (IL)

(*) Notice: Subject to any disclaimer, the term of this patent is extended or adjusted under 35 U.S.C. 154(b) by 0 days.

(21) Appl. No.: 09/623,227
(22) PCT Filed: Feb. 22, 1999
(86) PCT No.: PCT/IL99/00108
§ 371 (c)(1), (2), (4) Date: Oct. 31, 2000
(87) PCT Pub. No.: WO99/45516
PCT Pub. Date: Sep. 10, 1999

(30) Foreign Application Priority Data

Mar. 2, 1998 (IL) .................................................. 123516

(51) Int. Cl.[7] .............................................. G08B 13/14
(52) U.S. Cl. ...................... 340/568.7; 340/575; 600/500
(58) Field of Search ............................... 340/568.7, 575, 340/567, 566, 539, 531; 600/301, 481, 500, 509, 514; 379/37, 38

(56) References Cited

U.S. PATENT DOCUMENTS

| 3,082,414 A | * | 3/1963 | Papaminas ................ 340/575 |
| 4,622,544 A | | 11/1986 | Bially et al. |
| 5,058,597 A | | 10/1991 | Onoda et al. |
| 5,162,776 A | | 11/1992 | Bushnell et al. |
| 5,514,862 A | | 5/1996 | Salzano |
| 5,890,052 A | * | 3/1999 | Read et al. ................ 455/90 |
| 6,063,036 A | * | 5/2000 | Li .............................. 600/503 |

FOREIGN PATENT DOCUMENTS

| EP | 0 535 629 | 4/1993 |
| GB | 2 285 135 | 6/1995 |
| GB | 2 312 066 | 10/1997 |
| WO | 87 05137 | 8/1987 |

* cited by examiner

Primary Examiner—John Tweel
(74) Attorney, Agent, or Firm—Browdy and Neimark, P.L.L.C.

(57) ABSTRACT

An emergency signaling or diagnostic device (10), particularly with an ECG signaling device (11, 11') embedded within a wallet (35) for signaling a health condition of an owner of the device. The wallet (35) may have embedded therein functions (40) of a cellular telephone and may include a vocalizing unit (16) for producing an acoustic signal representative of the owner's ECG.

40 Claims, 4 Drawing Sheets

EMERGENCY SIGNALING OR DIAGNOSTIC DEVICE

CROSS REFERENCE TO RELATED APPLICATION

The present application is the national stage under 35 U.S.C. 371 of PCT/IL99/00108, filed Feb. 22, 1999.

FIELD OF THE INVENTION

This invention relates to portable electronic instruments for personal use and, in particular, to so-called Personal Emergency Response Systems.

BACKGROUND OF THE INVENTION

It is known that certain people are particularly vulnerable to attack or seizure such as, for example, the elderly and infirm. To this end, it is also known to provide such people with panic alarm devices so that at the onset of an attack, in whatever form that might be, or even in the event of imminent risk thereof, the panic alarm device may be manually operated so as call for help in time of need and inform a central monitoring unit. Upon receipt of a panic signal, the central monitoring unit may then take appropriate action. Panic alarm devices are, therefore, an important component in the arsenal of those who are vulnerable, thereby providing them with greater security and self-confidence.

Typically, such panic alarms include a manually operated r.f. transmitter energized by a miniature hearing-aid type battery and which, when operated, sends an encoded signal characteristic of the user. By such means, a remote monitoring unit, upon receiving the encoded signal, knows from where the signal emanated. Most simply, the coding can be by way of modulating an r.f. signal with data representative of the user's personal code so that the received signal is indicative of the sender. A problem associated with such devices is their accessibility. It clearly defeats the whole object of the device if, at a moment of panic, the device is not readily accessible for actuation and precious time must be wasted in locating it. To this end, such devices are commonly worn as a pendant around the owner's neck, which is liable to be both obtrusive and cumbersome.

It has also been proposed to provide such panic alarms in a wrist-mounted casing including a conventional watch movement, so that the device can double as both a conventional watch and a panic alarm. By such means, the same device serves two functions, thereby increasing its convenience and rendering the panic alarm function completely unobtrusive. In such a device, communication with the remote monitoring unit is effected via the telephone line and, to this end, there must be provided a base unit connected to the telephone line for effecting wireless communication with the portable device. This is acceptable when the patient is house-bound but is obviously unsuitable for those patients who are generally free to live normal lives but must nevertheless have ready access to the remote monitoring unit in case of emergency.

Upon effecting communication with the monitoring unit, a patient is frequently required to undertake an interactive dialog with medical personnel at the monitoring unit so as to enable the medical personnel to diagnose the patient's medical symptoms. Since many of those who are particularly at risk suffer from heart-disease, an ECG is usually one of the first tests which should be carried out. To this end, much effort has been directed to the provision of portable instruments for allowing a patient to carry out an ECG on himself. At their most rudimentary, such instruments comprises a pair of electrodes which are held against a patient's body, usually near his chest to detect an electrical voltage indicative of the electrical activity of the heart. The resulting current waveform response permits partial determination of the patient's cardiac health. A more detailed determination may be realized by using more than two electrodes and portable devices are known having, for example, twelve electrodes mounted on a common carrier and amenable to placement on a patient's chest area by the patient with minimum effort.

It will be appreciated that no less important than the technical suitability of such ECG transmitters, is that they must be instantly accessible in a moment of crisis. In the first instance, the required accessibility can only be realized by a portable device. However, experience indicates that this in itself is often not enough. Most people find it difficult to function and to preserve their mental health if they live in constant fear of their mortality. Particularly, those who have a history of heart disease or other serious illness can do without constant remainders that they might need to perform an instant ECG in the street or elsewhere remote from hospital or home. As a result, there are many who consign the thought to their sub-conscious and it is then but a small step to relegating it to their unconscious altogether.

Such a likelihood would be reduced if the ECG transmitter were not only portable but were so disguised as to be indistinguishable from an everyday item which, in any case, the patient would carry on his or her person. However, the prior art does not seem even to have addressed the problem associated with the almost wanton forgetfulness by the infirm, let alone propose a solution thereto.

SUMMARY OF THE INVENTION

This problem is solved in accordance with a broad aspect of the invention by means of an emergency signaling or diagnostic device integrally embedded within a wallet for signaling a health condition of an owner of the device.

According to a preferred embodiment, the emergency signaling or diagnostic device is an ECG transmitter having at least two electrodes sewn or otherwise fixed to a surface of the wallet and having controls accessible from inside the wallet. Such a wallet is provided with pockets for accommodating therein cash, credit cards and so on in known manner so that the patient who carries it is psychologically immune from the uncomfortable thought that anything medical is associated therewith.

In order to allow the patient to relay the ECG signal to a remote monitoring unit, a vocalizing unit may be provided for converting the ECG signal to a representative acoustic signal which can be sent over the telephone to the monitoring unit. Alternatively, the ECG signal may be modulated on to an r.f. carrier signal for direct transmission with the monitoring unit, thus not requiring that the patient be in ready access with a telephone.

BRIEF DESCRIPTION OF THE DRAWINGS

A preferred embodiment of the invention will now be described, by way of non-limiting example only, with particular regard a Personal Emergency Response System and with reference to the accompanying drawings, in which.

DETAILED DESCRIPTION OF PREFERRED EMBODIMENTS

Figure 1:
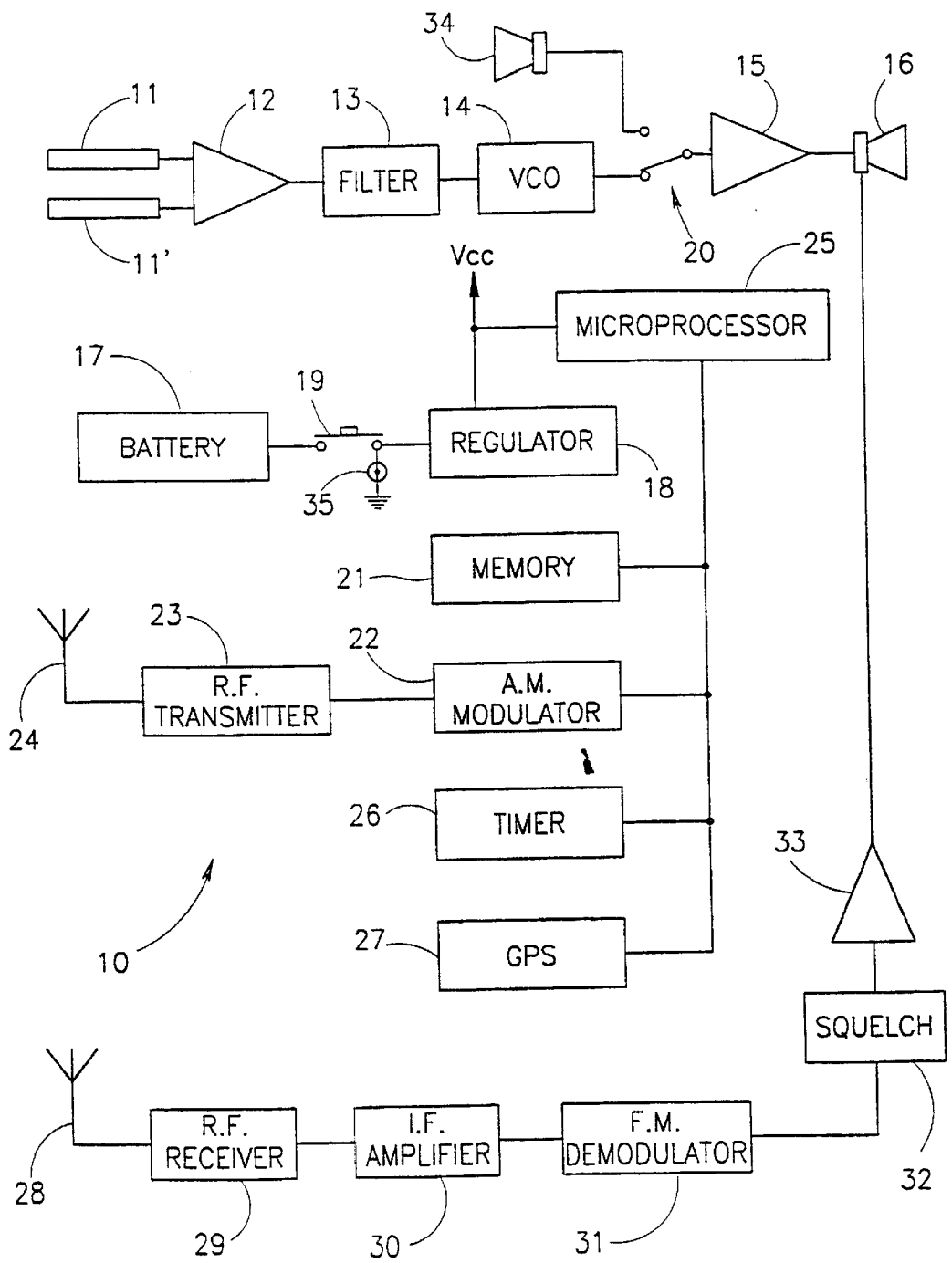
FIG. 1 is a block diagram showing functionally the principal components in a Personal Emergency Response System according to the invention.

FIG. 1 shows functionally a Personal Emergency Response System (constituting an emergency signaling device) depicted generally as 10, comprising a portable ECG signaling device having a pair of electrodes 11 and 11' for placing against a patient's bare chest and being coupled to an amplifier 12. The amplifier 12 is coupled to a filter 13 whose output is fed to a voltage controlled oscillator (VCO) 14 for converting the amplified and filtered ECG signal to an equivalent variable frequency voltage. The VCO 14 thus constitutes a frequency modulator for converting the analog ECG signal to a representative frequency signal centered around 1700 Hz and frequency modulated by the patient's ECG signal. The variable frequency voltage is fed via a first pole of a selector switch 20 to an audio amplifier 15 whose output may be fed to a loudspeaker 16, which together constitute a vocalizing unit for converting the ECG signal to an equivalent acoustic signal which may be fed over the telephone line to a remote monitoring unit (not shown).

The Personal Emergency Response System 10 is powered by means of an internal battery 17 comprising, for example, three CR 32 cells and being connected to a voltage regulator 18 via a normally open pushbutton switch 19. Depressing the pushbutton switch 19 thus connects a regulated battery voltage to the various components of the ECG signaling device 10 so that a modulated tone representative of an ECG rhythm strip is output by the loudspeaker 16 for so long as the pushbutton switch 19 is depressed. The three cells within the battery 17 may be removably mounted in a casing of the ECG signaling device 10 so as to be replaceable, or they may be irremovable in which case the ECG signaling device 10 must be discarded when the battery 17 is spent.

A memory 21 is coupled to an a.m. modulator 22 for amplitude modulating data stored in the memory 21 representative of a unique identity code of the patient as well as any other relevant data. By such means, the patient's personal data and identity may be amplitude modulated on to a carrier signal which is fed to an r.f. transmitter 23 coupled to an antenna 24. The memory 21 thus serves as an encoder for encoding the patient's personal identity code, it being understood that other encoding means can equally well be employed, such as, for example, DIP switches and so on.

A microprocessor 25 is coupled to the memory 21 for operating in accordance with an instruction set stored therein. A timer 26 (constituting a timer circuit) is coupled to the microprocessor 25 for providing timing signals thereto, the microprocessor 25 being responsive to the instruction set in the memory 21 and to the timing signals received from the timer 26 for terminating operation a predetermined time period after actuation thereof. The microprocessor 25 is further responsive to the timer 26 for initiating transmission with the remote monitoring unit at regular intervals of time so as to send an "I'm alive" signal at regular time intervals. By such means, even in the absence of manual actuation by the patient, the remote monitoring unit may be assured that the device is functional. Preferably, if the battery voltage is low, part of the transmitted signal is encoded so that the remote monitoring unit may be suitably apprised and take remedial action. Alternatively, the low voltage battery signal may be sent independent of the "I'm alive" signal.

It may be desirable for the Personal Emergency Response System 10 automatically to signal to the remote monitoring unit the exact spatial location of the patient so as to allow an ambulance to be dispatched quickly in the event that the patient is unable to speak. To this end, a GPS unit shown functionally as 27 is coupled to the microprocessor 25. The GPS unit 27 constitutes a spatial location determination unit for receiving GPS positional data via the antenna 24 and allowing it to be forwarded to the remote monitoring unit after suitable modulation on to the r.f. carrier signal.

In order to allow for bi-directional communication with the remote monitoring unit, there is further provided a receiving antenna 28 coupled to an r.f. receiver 29 an output of which is fed to an I.F. amplifier 30 whose output is coupled to a f.m. demodulator 31. An output of the f.m. demodulator 31 is fed in conventional manner to a squelch circuit 32 whose output is coupled via a second pole (not shown) of the selector switch 20 to an output amplifier 33 connected to the loudspeaker 16. A microphone 34 may be connected to the audio amplifier 15 allowing the patient to speak to a medical practitioner at the remote monitoring unit and to hear the medical practitioner through the loudspeaker 16.

Figure 2:
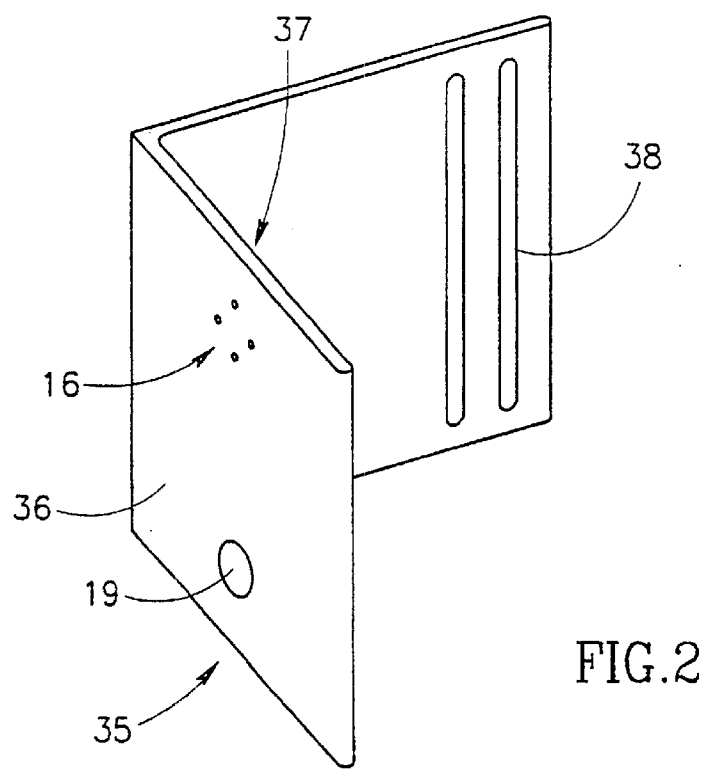
FIG. 2 shows pictorially the Personal Emergency Response System of FIG. 1 embedded within a wallet according to a first embodiment the invention.

Referring to FIG. 2, the Personal Emergency Response System 10 is shown accommodated within a wallet 35, the loudspeaker 16 and the pushbutton switch 19 being sewn or otherwise fixed to an outer surface 36 thereof. An inside surface 37 is provided in known manner with a plurality of pockets 38 for accommodating notes, credit cards and so on. The remaining circuitry is mounted on a flexible circuit board (not shown) which is secured between the outer and inner surfaces 36 and 37 of the wallet 35. The use of a flexible circuit board allows for the wallet 35 to be folded and subject to moderate deformation as may be applied when the wallet 35 is placed, for example, in a patient's rear trouser pocket and is thereby subject to deformation whenever the patient sits down.

Figure 3:
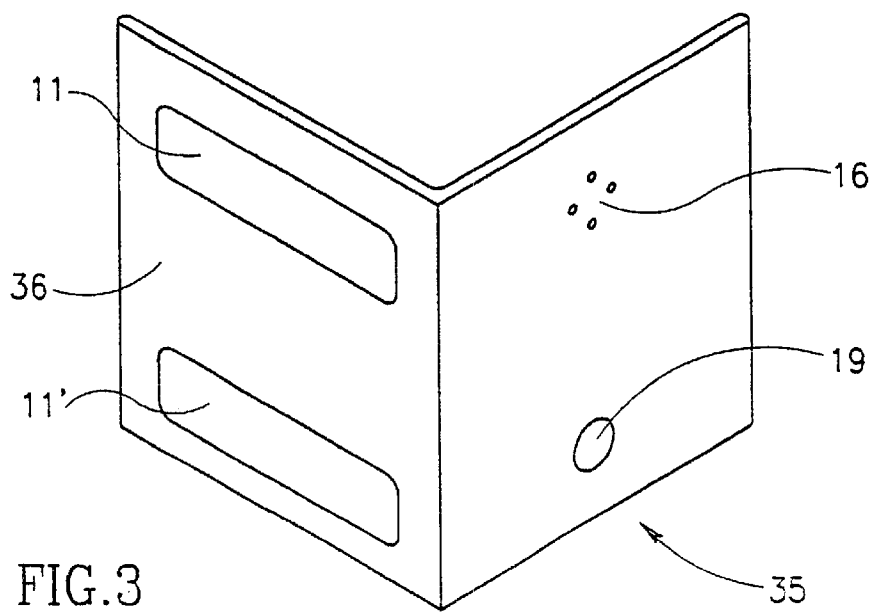
FIG. 3 shows pictorially an ECG signaling device embedded with a wallet.

Referring to FIG. 3, there is shown accommodated within a wallet 35 only an ECG signaling device whose electrodes 11 and 11' are sewn or otherwise fixed to a first outer surface 36 thereof. The loudspeaker 16 and the pushbutton switch 19 are mounted within the outer and inner surfaces 36 and 37 of the wallet 35 so as to be accessible from the outer surface 36. The remaining circuitry is mounted on a flexible circuit board (not shown) which is secured between the outer and inner surfaces 36 and 37 of the wallet 35. In use, and in the absence of the autonomous wireless transmission means constituted by the r.f. transmitter 23 shown in FIG. 1, the patient must first approach a telephone and dial the remote monitoring unit. Connection having been established, he now places the electrodes 11 and 11' in position and activates the device by depressing the pushbutton switch 19. As noted above, this produces an acoustic signal representative of the ECG rhythm strip and the acoustic signal is transmitted over the telephone line in the usual way.

Figure 4:
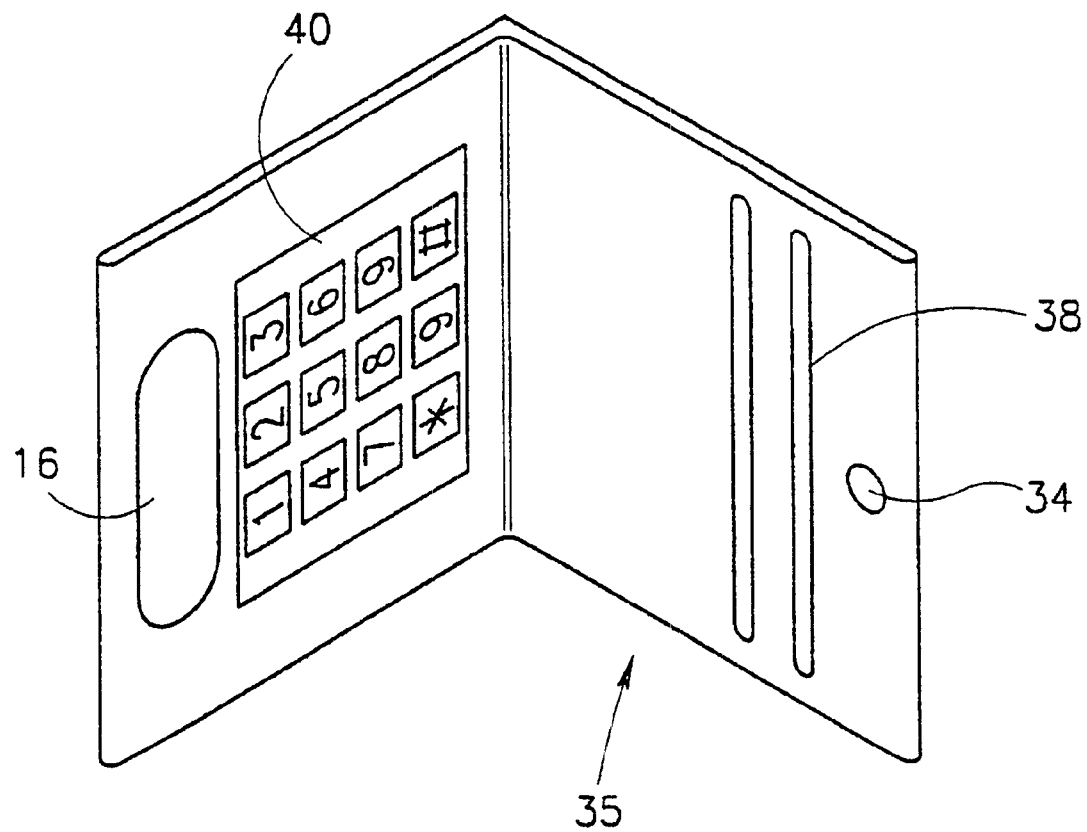
FIG. 4 shows pictorially a detail of a wallet serving as a cellular telephone and having embedded therein a Personal Emergency Response System or an ECG signaling device.

FIG. 4 shows schematically the wallet 35 having embedded herein an emergency signaling device and sharing the functions of a miniature cellular telephone. To this end, there is provided an antenna (not shown) in the spine of the wallet.

The antenna may be either of fixed, inextendible length or may be telescopic in which case a small part of the antenna may protrude from the wallet to facilitate extraction thereof. A keypad 40 and display (not shown) may be provided on the inner surface 37 of the wallet, these features being well known per se and therefore not requiring further elaboration.

In the event that the emergency signaling device embedded within the wallet 35 is an ECG signaling device, the electrodes 11 and 11' may be fixed to the outer surface 36 of the wallet 35 as shown in FIG. 3. The pushbutton switch 19 may be duplicated by one of the conventional keys, such as the SEND or TRANSMIT buttons of the cellular telephone. Likewise, the loudspeaker 16 and the microphone 34 may duplicate the conventional components of the cellular telephone.

Figure 5:
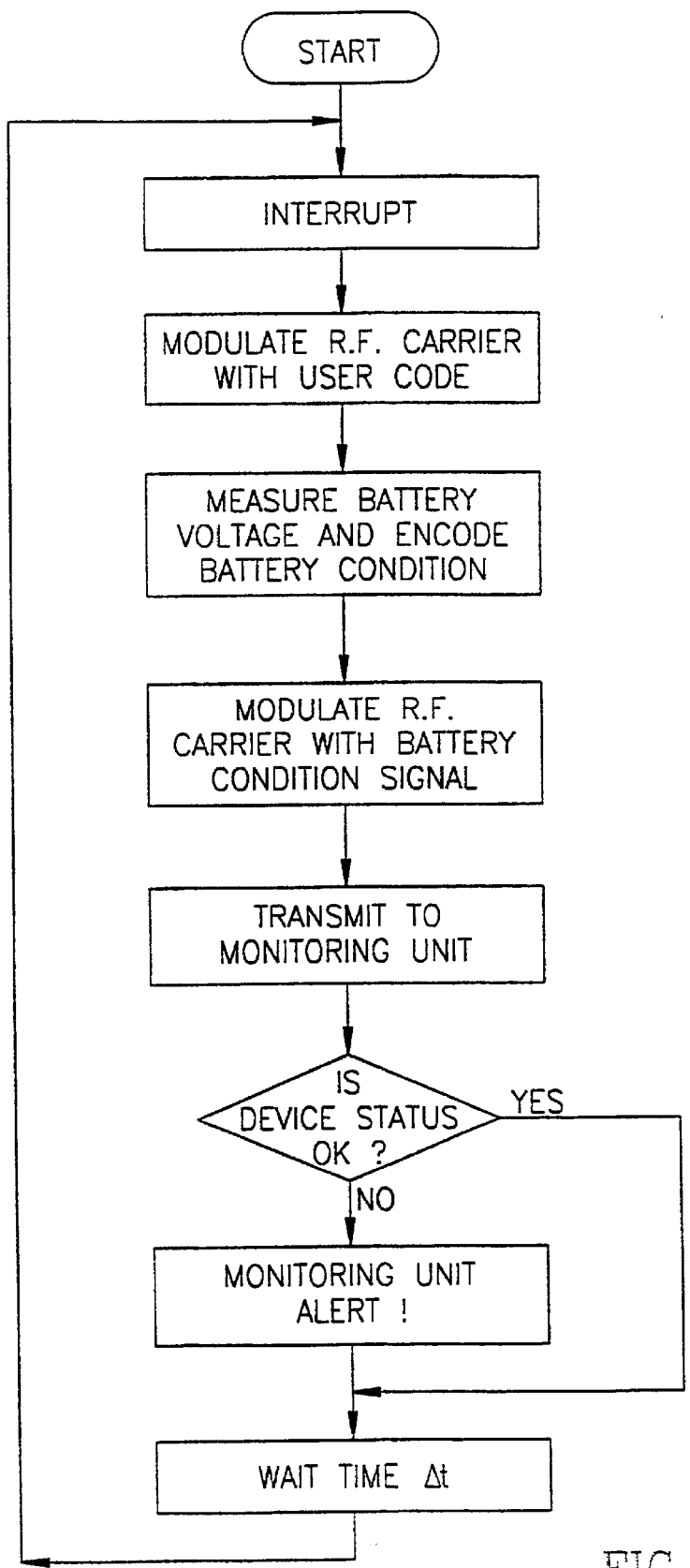
FIG. 5 is a flow diagram showing the principal operating steps for use with a microprocessor in the device.

FIG. 5 shows the principal operating steps associated with the instruction set stored in the memory 21 for controlling the microprocessor 25. The microprocessor 25 is responsive to an interrupt signal that is produced whenever the pushbutton switch 19 is depressed. The interrupt signal is also produced at regular time intervals based on the timing signal produced by the timer 26. When the pushbutton switch 19 is depressed so as to actuate the device, the user identity code stored in the memory 21 is fetched by the microprocessor 25 and fed to the a.m. modulator 22 which modulates the r.f. carrier signal therewith so as to send an a.m. signal via the antenna 24 to the remote monitoring unit. A signal, representative of the voltage of the battery 17, is fed to the microprocessor 25 that determines the condition of the battery therefrom and generates a corresponding battery condition signal. The r.f. carrier signal is frequency modulated with the battery condition signal so as likewise to be transmitted to the remote monitoring unit. It should be understood that the battery condition signal is merely representative of the normal operating condition of the device, it being contemplated that other signals representative of the device status may be measured, thus allowing the r.f. carrier signal to be modulated therewith and providing the monitoring unit with a full picture of the device operability.

Thus, upon the antenna 24 receiving the r.f. signal, the remote monitoring unit determines whether the device status is O.K. and, if not, takes suitable remedial action. In the absence of further pressure on the pushbutton switch 19, a predetermined time interval is measured by the timer 26, when a further interrupt is generated and the cycle repeats.

Preferably, successively depressing the pushbutton switch 19 alternatively actuates and deactuates the device. Likewise, the microprocessor 25 is preferably responsive to the timer 26 for disabling deactuation of the device for a predetermined time period following actuation thereof. For example, following actuation of the device by pressing the pushbutton switch 19, further depression thereof within a time window of three seconds has no effect. Furthermore, preferably deactuation within a predetermined time period is effected by means of sustained pressure on the pushbutton switch 19. These factors may be important when the device is used by the elderly or infirm, so as to guard against the effect of finger shake.

Upon actuating the device, an a.m. r.f. signal is transmitted to the remote monitoring unit where the user's unique identity is decoded. Once communication has been established, the user chooses the correct setting of the selector switch 20 so as to connect the microphone 34 to the amplifier 15. The user may now speak into the microphone 34 so as to frequency modulate the r.f. signal, the resulting modulated carrier signal being transmitted to the remote monitoring unit. By such means, the user of the device 10 may converse with a medical practitioner situated remotely at the monitoring unit site. Alternatively, when it is desired to transmit the ECG rhythm strip, the selector switch is set to the other position, so as to connect the VCO 14 to the amplifier 15.

An LED 35 is coupled to the pushbutton switch 19 so as to be illustrated when the pushbutton switch is closed, thereby providing a visual indication of the operation of the device.

It will be appreciated that modifications and variations may be effected to the preferred embodiments without departing from the spirit of the invention. Thus, for example, whilst the invention has been described with particular reference to a Personal Emergency Response System, it will be understood that such a system contains many features which can be dispensed with if bi-directional communication with the monitoring unit is not required. In such case, for example, a wallet may be provided with only the ECG signaling device and a transmitter for transmitting the ECG rhythm strip to the remote monitoring unit together with a signal encoding the user's ID and location. If a microphone is provided, then there is no need to encode either the user's ID or location since he can direct the remote monitoring unit as to his identity and whereabouts. Thus obvious design variations can be implemented according to individual requirement.

Likewise, different modulation techniques may be employed as are well known in the art. The battery condition signal may be sent together with the "I'm alive" signal or independent thereof, and so on. Other common household articles may be adapted to incorporate therein the ECG signaling device or, indeed, other electronic devices so as to serve a dual purpose, thereby increasing the likelihood that their owner will wish to make use thereof. It will also be understood, as noted above, that whilst the ECG signaling device shown in the preferred embodiment has two electrodes, this is not a feature of the invention which contemplates the use of ECG signaling devices having more than two electrodes. It will also be appreciated that it is immaterial whether the ECG electrodes are fixed to an interior or exterior surface of the wallet.

What is claimed is:

1. An emergency signaling or diagnostic device (10) integrally embedded within a wallet (35) for signaling a health condition of an owner of the device.

2. The device according to claim 1, wherein the wallet (35) has embedded therein functions (40) of a cellular telephone.

3. The device according to claim 1, comprising an ECG signaling device (11, 11').

4. The device according to claim 3, including a vocalizing unit (16) for producing an acoustic signal representative of the owner's ECG.

5. The device according to claim 1, being a Personal Emergency Response System (10).

6. The device according to claim 1, for relaying data associated with the owner of the device to a remote monitoring unit, the device comprising:
   an r.f. transmitter (23) coupled to an antenna (24) and a battery (17) and mounted within a casing (36, 37) of the wallet,
   an identification unit (21, 27, 34) for relaying a personal identity and spatial location of the owner of the device, and
   a modulator (22) coupled to the r.f. transmitter (23) for modulating an r.f. carrier signal with said data.

7. The device according to claim 6, wherein the identification unit comprises:
a processor (25),
an encoder (21) coupled to the processor (25) for encoding the personal identity of the owner of the device, and
a spatial location determination unit (27) coupled to the processor (25) for providing a signal indicative of a spatial location of the device.

8. The device according to claim 6, further including a visual indication device (35) coupled to the battery (17) via an actuator (19) for providing a visual indication of an actuation of the device.

9. The device according to claim 6, wherein:
the identification unit comprises a microphone (34) for receiving a voice signal for allowing the owner of the device to recite his identity and/or spatial location.

10. The device according to claim 6, including a processor (25) which is responsive to a battery condition signal representative of a condition of the battery (17) for modulating the r.f. signal with said battery condition signal so as to inform the monitoring unit accordingly.

11. The device according to claim 10, wherein the processor (25) is responsive to a voltage of the battery being lower than a predetermined threshold for automatically transmitting the r.f. signal.

12. The device according to claim 7, further including a timing circuit (26) coupled to the processor (25) for terminating operation thereof a predetermined time period after initiation of the actuator.

13. The device according to claim 7, further including a timing circuit (26) coupled to the processor (25) for transmitting an "I'm alive" signal for relaying to the remote monitoring unit at predetermined intervals of time.

14. The device according to claim 8, wherein the actuator is a manual pushbutton switch (19).

15. The device according to claim 14, wherein successively depressing the pushbutton switch alternately actuates and deactuates the device.

16. The device according to claim 13, including a manually operated switch (19) for actuating and de-actuating the device and wherein:
the processor (25) is responsive to the timing circuit (26) for disabling deactuation of the device for a predetermined time period following actuation thereof.

17. The device according to claim 16, wherein the processor (25) is further responsive to the timing circuit (26) for actuating only when the manually operated switch (19) is operated for longer than a predetermined time period.

18. The device according to claim 6, further including:
a receiving antenna (28) for receiving an r.f signal from the remote monitoring unit,
an r.f. receiver (29) coupled to the receiving antenna and having an output fed to an I.F. amplifier (30),
a demodulator (31) coupled to an output of the r.f. receiver and having an output fed to a squelch circuit (32),
an audio amplifier (33) coupled to an output of the squelch circuit and being connected to a loudspeaker (16).

19. The device according to claim 6, including:
a microphone (34) switchably connected to an input of an audio amplifier (15) having a loudspeaker (16) connected to an output thereof for allowing the owner to speak to a medical practitioner at the remote monitoring unit and to hear the medical practitioner through the loudspeaker.

20. The device according to claim 6, being mounted on a flexible circuit board.

21. An ECG signaling device in combination with a wallet, wherein: said device is integrally embedded within said wallet; and said device comprises at least two chest electrodes fixed to a surface of said wallet and arranged to be placed against a user's chest when it is required to produce an ECG signal.

22. The device of claim 21, further comprising an actuating button fixed in said wallet and actuatable by the user for placing said device into operation.

23. The device according to claim 21, wherein the wallet has embedded therein functions of a cellular telephone.

24. The device according to claim 21, including a vocalizing unit for producing an acoustic signal representative of the owner's ECG.

25. The device according to claim 21, being a Personal Emergency Response System.

26. The device according to claim 21, for relaying data associated with the owner of the device to a remote monitoring unit, the device comprising:
an r.f. transmitter coupled to an antenna and a battery and mounted within a casing of said wallet,
an identification unit for relaying a personal identity and spatial location of the owner of the device, and
a modulator coupled to the r.f. transmitter for modulating an r.f. carrier signal with said data.

27. The device according to claim 26, wherein the identification unit comprises:
a processor,
an encoder coupled to the processor for encoding the personal identity of the owner of the device, and
a spatial location determination unit coupled to the processor for providing a signal indicative of a spatial location of the device.

28. The device according to claim 26, further including a visual indication device coupled to the battery via an actuator for providing a visual indication of an actuation of the device.

29. The device according to claim 26, wherein:
the identification unit comprises a microphone for receiving a voice signal for allowing the owner of the device to recite his identity and/or spatial location.

30. The device according to claim 26, including a processor which is responsive to a battery condition signal representative of a condition of the battery for modulating the r.f. signal with said battery condition signal so as to inform the monitoring unit accordingly.

31. The device according to claim 30, wherein the processor is responsive to a voltage of the battery being lower than a predetermined threshold for automatically transmitting the r.f. signal.

32. The device according to claim 27, further including a timing circuit coupled to the processor for terminating operation thereof a predetermined time period after initiation of the actuator.

33. The device according to claim 27, further including a timing circuit coupled to the processor for transmitting an "I'm alive" signal for relaying to the remote monitoring unit at predetermined intervals of time.

34. The device according to claim 28, wherein the actuator is a manual pushbutton switch.

35. The device according to claim 34, wherein successively depressing the pushbutton switch alternately actuates and deactuates the device.

36. The device according to claim 33, including a manually operated switch for actuating and de-actuating the device and wherein:

the processor is responsive to the timing circuit for disabling deactuation of the device for a predetermined time period following actuation thereof.

37. The device according to claim 36, wherein the processor is further responsive to the timing circuit for actuating only when the manually operated switch is operated for longer than a predetermined time period.

38. The device according to claim 26, further including:

a receiving antenna for receiving an r.f signal from the remote monitoring unit, an r.f. receiver coupled to the receiving antenna and having an output fed to an I.F. amplifier, a demodulator coupled to an output of the r.f. receiver and having an output fed to a squelch circuit, an audio amplifier coupled to an output of the squelch circuit and being connected to a loudspeaker.

39. The device according to claim 26, including:

a microphone switchably connected to an input of an audio amplifier having a loudspeaker connected to an output thereof for allowing the owner to speak to a medical practitioner at the remote monitoring unit and to hear the medical practitioner through the loudspeaker.

40. The device according to claim 26, being mounted on a flexible circuit board.

* * * * *